(12) United States Patent
Iddan et al.

(10) Patent No.: US 8,105,280 B2
(45) Date of Patent: Jan. 31, 2012

(54) DISPOSABLE DISPENSER FOR PATIENT INFUSION

(75) Inventors: Gavriel J. Iddan, Haifa (IL); Avishai Friedman, Caesarea (IL); Ofer Yodfat, Maccabim-Reut (IL)

(73) Assignee: Medingo, Ltd., Yoqneam Illit (IL)

( * ) Notice: Subject to any disclaimer, the term of this patent is extended or adjusted under 35 U.S.C. 154(b) by 1011 days.

(21) Appl. No.: 11/920,469

(22) PCT Filed: May 14, 2006

(86) PCT No.: PCT/IL2006/000569
§ 371 (c)(1),
(2), (4) Date: Feb. 12, 2008

(87) PCT Pub. No.: WO2006/123329
PCT Pub. Date: Nov. 23, 2006

(65) Prior Publication Data
US 2008/0234630 A1  Sep. 25, 2008

(30) Foreign Application Priority Data

May 17, 2005 (IL) .......................................... 168642

(51) Int. Cl.
*A61M 37/00* (2006.01)
(52) U.S. Cl. ...................................................... 604/131
(58) Field of Classification Search .......... 604/131–155, 604/890.1, 891.1, 892.1, 181, 187
See application file for complete search history.

(56) References Cited

U.S. PATENT DOCUMENTS

| | | | | |
|---|---|---|---|---|
| 4,684,368 A | * | 8/1987 | Kenyon | 604/152 |
| 5,961,492 A | | 10/1999 | Kriessel et al. | |
| 6,656,158 B2 | * | 12/2003 | Mahoney et al. | 604/131 |
| 6,960,192 B1 | * | 11/2005 | Flaherty et al. | 604/181 |
| 2002/0040208 A1 | * | 4/2002 | Flaherty et al. | 604/288.01 |

FOREIGN PATENT DOCUMENTS

WO  WO 03/090509 A2  11/2003

OTHER PUBLICATIONS

International Search Report, PCT Application No. PCT/IL2006/000569, date of mailing Apr. 3, 2007.

* cited by examiner

*Primary Examiner* — Matthew F Desanto
(74) *Attorney, Agent, or Firm* — Mintz Levin Cohn Ferris Glovsky and Popeo, P.C.

(57) ABSTRACT

Embodiments of the invention are directed to methods and systems associated with a disposable dispenser (100, 200) of therapeutic fluid. Preferred embodiments having a small size of less than about 75 mm in length, less than 50 mm in width and less than about 10 mm in thickness and may be releasably attached to the body (B). In one embodiments, the dispenser draws fluid from a flexible volume-conformable reservoir (4) and operates a dosing and metering pump (6, 61, 62, 63) incorporating a motor to deliver fluid through a fluid delivery tool (8, 81, 82). Disposed on the housing bottom (2B) is a peel-off tape (22) that when removed, electrically connects a power supply (18) to power the operative components (3) of the dispenser into operation, exposes an adhesive (28) and a window (21) in the housing (2), and allows the fluid delivery tool (8) to extend for insertion into the skin (S).

19 Claims, 7 Drawing Sheets

DISPOSABLE DISPENSER FOR PATIENT INFUSION

CROSS REFERENCE TO RELATED APPLICATIONS

This application claims benefit to PCT application no. PCT/IL2006/000569, having an international filing date of May 14, 2006, and Israel Patent Application No. 168642, filed May 17, 2005. Each of the foregoing disclosures is expressly incorporated herein in its entirety.

TECHNICAL FIELD

The present invention relates to a method for implementing a system and a disposable dispenser for personal use, and more specifically, a low-cost, small volume programmable dispenser for infusion of therapeutic fluid.

BACKGROUND ART

Diabetes mellitus patients require the administration of varying amounts of insulin throughout the day in order to control their blood glucose levels. In recent years, ambulatory insulin infusion pumps have emerged as a superior alternative to multiple daily injections of insulin. These pumps, which deliver insulin subcutaneously at a continuous basal rate as well as in bolus volumes, were developed in order to free patients of the need to repeatedly self-administer injections and allow them to maintain a near-normal routine. Furthermore, continuous subcutaneous infusion of insulin produces better insulin pharmacokinetics than multiple daily injections, resulting in better regulation of blood glucose levels.

There are several ambulatory insulin infusion devices currently in the market. These devices are reusable since they are provided with a refillable reservoir for insulin. These reusable devices represent a significant improvement over multiple daily injections, but they suffer from several drawbacks: they are expensive, bulky, fragile and difficult to program and fill the reservoir.

The prior art mentions multiple attempts to devise insulin diffusion systems fitted with disposable programmable dispensers for personal use by a patient. Such systems are described, for example, in U.S. Pat. Nos. 6,740,059, 6,749,587, 6,960,192, and in US Published Patent Applications No. 20050203461, 20050021005, 20040204673.

Nevertheless, despite these many attempts there still exists an acute need for a new and improved system, which employs a disposable programmable dispenser for the continuous infusion of insulin or of other therapeutic fluids.

DISCLOSURE OF INVENTION

Accordingly, embodiments of the present invention address the above-noted concern and present a method for implementing a dispenser of therapeutic fluid that is smaller than a plastic credit card. Specifically, in one embodiment of the present invention, a fluid dispenser having an overall size of about half that of an ordinary credit-card and being less than about four times the thickness of a credit-card. Moreover, some embodiments of the present invention present a fluid dispenser which is preferably flexible, body conformable, and adhesively attachable to the body of the user. Such may be achieved by adopting a thin flat planar layout of dispenser components, including (preferably) a flat motor and pump construction, designed for inexpensive manufacture, automatic assembly. Moreover, some embodiments of the invention are designed for safe discarding, thereby providing a disposable device.

Some embodiments of the present invention are directed to a system for the continuous infusion of insulin or another therapeutic fluid. Such a system may include an accurate and safe disposable programmable dispenser, but is simultaneously small, lightweight, easy-to-use and inexpensive.

Accordingly, it is an object of some of the embodiments of the present invention to provide a method for implementing a thin flat planar disposable dispenser infusing a therapeutic fluid through the skin into the body of a user, comprising a programmable controller for control, management and operation of the dispenser, and operable by the user with or without remote control.

It is another object of some of the embodiments of the present invention to provide a method for implementing a disposable dispenser having a housing configured into a normal parallelepiped having dimensions of about 75 mm or less in length (preferably about 50 mm), 60 mm or less in width (preferably about 30 mm) and about 10 mm or less in thickness (preferably about 4 mm), including (in some embodiments) a flexible volume-conformable reservoir filled with therapeutic fluid contained within the housing interior.

It is a further object of some of the embodiments of the present invention to provide a method for including, within the housing interior, a thin flat planar dosing and metering pump which preferably incorporates a motor, with the pump preferably being coupled in fluid communication with and downstream (for example) of, the reservoir to deliver sequential unit doses of therapeutic fluid at a controlled flow rate via a downstream disposed fluid delivery tool.

It is yet an object of some of the embodiments of the present invention to provide a method for enabling operative components on a disposable dispenser device. Specifically, in one embodiment, a peel-off tape is removed from the bottom of the unit (for example) which not only allows electrical connection of a power supply (e.g., batteries) to power the operative components of the dispenser into operation, but may also expose an adhesive for attaching the dispenser to the skin of a user and establishes an opening, or a window in the housing to enable a fluid delivery tool to deploy for insertion into the skin of the user.

It is still another object of some of the embodiments of the present invention to provide a disposable dispenser having a dosing and metering pump implemented as a single-gear pump with a counter plate and has a flat layout and a sheet-like planar configuration.

It is yet a further object of some of the embodiments of the present invention to provide a disposable dispenser having a dosing and metering pump implemented as either one of both of an electromagnetic membrane pump and a gear-on-gear pump, and is embodied in flat layout and in sheet-like planar configuration.

It is yet a further object of some of the embodiments of the present invention to provide a disposable dispenser having a dosing and metering pump controllable to deliver predetermined single quantum unit doses and/or sequential successive single quantum unit doses, with single minute unit quantum doses of predetermined volume as small as 10 nanoliters.

It is yet a further object of some of the embodiments of the present invention to provide a disposable dispenser having a dosing and metering pump implemented as a single gear peristaltic pump with a plurality of magnetic rotors embedded therein in distribution, and with a plurality of electric drive coils appropriately distributed within the housing interior in operative association with the plurality of magnetic rotors.

The electric drive coils are operated under control and command of the programmable controller to drive the single gear into rotation at a controlled speed of rotation, and a quantum unit dose is predetermined according to the configuration of the gear and of the speed of rotation imparted to the single gear.

It is yet a further object of some of the embodiments of the present invention to provide a disposable dispenser having a dosing and metering pump implemented as a peristaltic pump with a single gear carrying a distribution of gear teeth, and with a predetermined controlled dose of therapeutic fluid quantum unit being delivered by the dispenser according to the distribution, configuration, and dimensions of gear teeth including width of the single gear.

It is yet a further object of some of the embodiments of the present invention to provide a disposable dispenser having a dosing and metering pump that is driven by a dish motor of flat shape.

It is yet a further object of some of the embodiments of the present invention to provide a disposable dispenser having a rotor position sensor that is disposed within the housing interior in operative association with the pump, with the rotor position sensor being appropriately coupled to a programmable controller to derive the flow rate of the therapeutic fluid.

It is yet another object of some of the embodiments of the present invention to provide a disposable dispenser having at least two pressure sensors that are disposed within a housing interior of the dispenser, spacially arranged downstream of a pump and upstream of a fluid delivery tool, where the at least two pressure sensors are preferably coupled to a programmable controller to derive either one or both of a fluid flow rate and fluid flow pressure.

It is yet further an additional object of some of the embodiments of the present invention to provide a disposable dispenser having a dosing and metering pump that is insensitive to backpressure variations.

It is yet still another object of some of the embodiments of the present invention to provide a disposable dispenser having a shut-off valve disposed within a housing interior of the dispenser to prevent leakage of the therapeutic fluid to the housing exterior when the dispenser is inoperative.

It is yet another object of some of the embodiments of the present invention to provide a disposable dispenser having operative components that are appropriately configured and disposed in a planar flat layout to minimize external dimensions of a housing of the dispenser, and having mounting seats that are provided within the housing interior to support and receive the operative components.

It is still another object of some of the embodiments of the present invention to provide a disposable dispenser having a remote control device that communicates with a programmable controller of the dispenser over a wireless bidirectional communication channel for controllable operation and for communication of interactive data, commands, and instructions to and from the dispenser.

It is an additional object of some of the embodiments of the present invention to provide a disposable dispenser having a remote control device including a remote control transceiver operating via a bi-directional communication channel for interactive communication with a programmable controller of the dispenser, and having a remote control I/O user interface disposed on the transceiver and operable by the user for entering and receiving data, instructions and commands, respectively, to and from the programmable controller.

It is yet an additional object of some of the embodiments of the present invention to provide a disposable dispenser that, prior to use, is packaged in a box having a removable cover, and in use, the cover is removed from the box and the dispenser retrieved out of the box. Thereafter, a fluid delivery tool unfolds and deploys to protrude to an exterior of a housing of the dispenser, ready for insertion into the body.

It is further an additional object of some of the embodiments of the present invention to provide a disposable dispenser that may be safely stored and removed from packaging. Specifically, according to one embodiment, a front side of a housing of the dispenser is placed into a packaging box, whereby a fluid delivery tool is in a stowed position along the bottom face of the housing.

It is still an additional object of some of the embodiments of the present invention to provide a disposable dispenser having a metallic ring (66) with a predetermined thermal mass that is arranged around an opening in a bottom face of a housing of the dispenser, and cooled prior to application and use of the dispenser. Application of the dispenser with the cooled metallic ring in contact with the skin (S) eases pain caused by insertion of the fluid delivery tool.

It is still further an additional object of some of the embodiments of the present invention to provide a disposable dispenser having a thin flat planar configuration and preferably including a disposable configuration. The dispenser may be used for infusing a therapeutic fluid through the skin into the body of a user, the dispenser including a housing with a housing top face, a housing bottom face, a housing exterior, and a housing interior accommodating therein operative components. The dispenser may also comprise an electronic circuit disposed within the housing interior and include a programmable controller for control, management and operation of the dispenser, and a transceiver operating a wireless bidirectional communication channel coupled to the programmable controller, the transceiver receiving and transmitting data and commands, as well as a fluid delivery tool disposed at a housing front side within the housing interior, the fluid delivery tool being coupled to a pump upstream and being inserted via an opening/window in the housing bottom face through the skin into the body of the user to deliver controlled doses of therapeutic fluid. In one embodiment, the method and the disposable dispenser are characterized by:

the housing being configured into a normal parallelepiped having dimensions of about 50 mm in length, 30 mm in width and 4 mm in thickness, a flexible volume-conformable reservoir filled with therapeutic fluid and disposed within the housing interior, a planar dosing and metering pump disposed within the housing interior and incorporating a motor, the pump being coupled in fluid communication with and downstream of the reservoir, to deliver sequential unit doses of therapeutic fluid at a controlled flow rate via the downstream disposed fluid delivery tool, a peel-off tape disposed on the housing bottom that when removed, electrically connects the power supply to power the operative components of the dispenser into operation, exposes an adhesive and an opening in the housing to allow the fluid delivery tool to deploy for insertion through the skin, whereby upon removal of the peel-off tape and application of the adhesive onto the skin, the dispenser is coupled to the body via the fluid delivery tool, in controlled infusion dosage delivery.

BRIEF DESCRIPTION OF DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

MODES OR CARRYING OUT THE INVENTION

A system including a disposable medication dispenser is described with reference to FIGS. 1-4. The system 1000 includes a fluid delivery device (dispenser 100) that preferably includes at least one of and preferably several or all of the following characteristics: thin, flat, planar, programmable, accurate, reliable and disposable.

Figure 1:
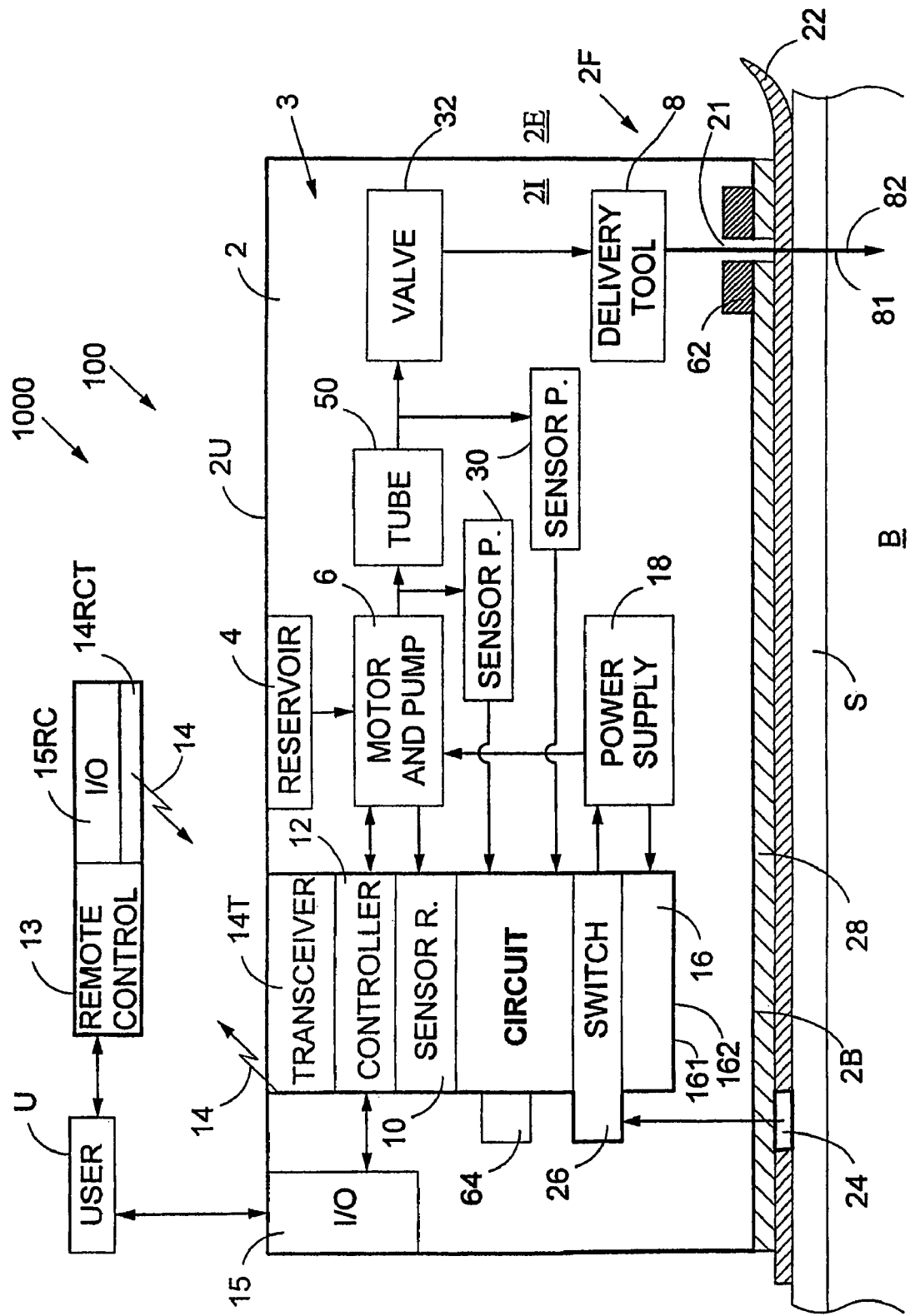
FIG. 1 is a schematic block diagram of a disposable fluid dispenser according to some embodiments of the present invention.

FIG. 1 is a block diagram showing the main operative components 3 of the dispenser 100, which has a plastic housing 2 and may include the following operative components:

a. A power supply (power source 18), such as environmentally-friendly silver oxide batteries, providing power to and energizing the operative components 3 of the dispenser 100.

b. A flexible volume-conformable reservoir 4 for containing the fluid to be infused, such as any therapeutic fluid, e.g. insulin or any other fluid substance.

c. A fluid delivery tool 8 for subcutaneous insertion of a trocar 81 and plastic cannula 82, into the skin S of a user U.

d. A thin, flat, planar controllable positive displacement pump 6 capable of administering controlled doses of the therapeutic fluid, preferably in predetermined single quantum unit doses and/or in sequential successive single quantum unit doses at a desired flow rate. The pump 6, which may also be referred to as a pump and metering system 6, is coupled in fluid communication to the reservoir 4 which is preferably disposed upstream thereof, and to the fluid delivery tool 8 that is preferably disposed downstream thereof. In such an arrangement, the pump 6 is thus disposed downstream of the reservoir 4 and upstream of the fluid delivery tool 8.

e. An electronic circuit 16, such as a printed circuit board 161, or PCB 161, or an integrated circuit 162 on which are preferably disposed the following:

i. A programmable controller 12 controlling the flow rate of dispensed fluid, according to preprogrammed instructions, or to instructions received from an external portable remote control device 13, or to instructions received through a user interface unit 15 which is optionally disposed on the external housing top face 2U, thus on the surface of the dispenser 100 facing away from the skin S. The programmable controller 12 also preferably manages, commands and controls the operation of the dispenser 100.

ii. A transceiver 14T receiving and transmitting data, commands and instructions. The transceiver 14T preferably operates a digital bi-directional communication channel 14 for receiving commands and instructions from the remote control device 13, for the delivery of those instructions to the programmable controller 12 to which it is coupled, and/or for receiving dispenser 100 status data from the controller 12 and transmitting the status data to the remote control device 13.

The remote control device 13 may be configured for communication with the programmable controller 12 over the wireless bi-directional communication channel 14 for controllable operation and for interactive data, commands, and instructions communication with the dispenser 100. Advantageously, the digital communication channel 14 may incorporate an error correcting code algorithm to protect the communicated data and commands from noise and interference.

In an alternative embodiment, the controller 12 and the transceiver 14T are integrated and disposed on an electronic circuit 16 implemented as a silicon wafer, thus as an integrated circuit, or IC, to enhance miniaturization of the dispenser 100 and reduce manufacturing costs.

In addition to the operative components 3 mentioned hereinabove and if desired, the housing 2 may host further optional operative components, like for example:

I. A rotor position sensor 10 operating in association with the positive displacement pump 6 for use when the pump 6 is a gear pump, as will be described hereinbelow. The rotor position sensor 10 is disposed either on the electronic circuit 16 as shown in FIG. 1, or elsewhere within the housing interior 2I, which last disposition is not shown in FIG. 1. The rotor position sensor 10 is appropriately coupled to the programmable controller 12 to derive the flow rate of the therapeutic fluid.

II. Two or more pressure sensors 30 which may be implemented in Micro-Electro-Mechanical Systems' technology, or MEMS.

III. A shut-off valve 32.

IV. Appropriate switches, one of which is designated by numeral 26 shown in FIG. 1.

V. A user interface unit 15 implemented as an Input/Output unit, or I/O unit, with various optional input and output components, such as a keyboard, a display optionally incorporated into the external top face 2U of the housing 2, and suitable for operating in bi-directional communication with the controller 12. The I/O unit may include components selected alone and in combination from the components consisting of a keyboard, a display, at least one alarm sounding device, and at least one light-emitting device LED.

Figure 2:
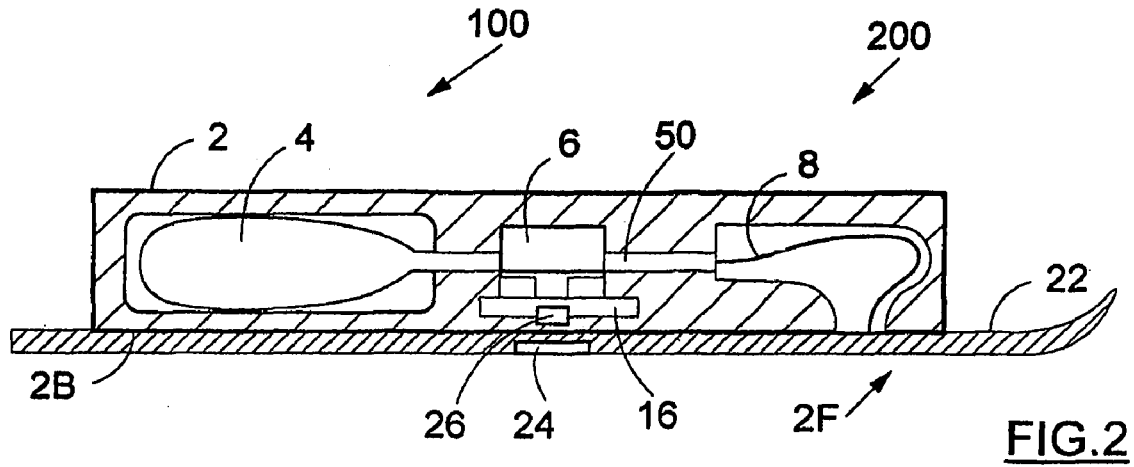
FIG. 2 shows a sectional side view of the dispenser of FIG. 1 before infusion.

FIG. 2 is a sectional side view of an exemplary embodiment 200 of the dispenser 100 before the initiation of therapeutic fluid infusion. At this stage, the external face of the housing bottom 2B of the housing 2 is covered with a peel-off tape 22 adhering to the housing 2 by virtue of an adhesive such as a biocompatible adhesive 28, applied as a layer to the housing bottom 2B. The fluid delivery tool 8 is implemented as a cannula 82, driven into the skin S by a trocar 81, possibly a hollow trocar 81. The fluid delivery tool 8 is kept in the housing interior 21, in extended or in a folded state.

A magnetic reed switch 26 may be disposed in the housing 2 in operative associated relationship with a magnet 24, which is sealed within the peel-off tape 22. The magnetic reed switch 26 is disposed either on the electronic circuit 16 as shown in FIG. 1, thus on the PCB 161 or on the integrated circuit 162, or elsewhere in the housing 2. As long as the peel-off tape 22 adheres to the housing 2, the magnet 24 keeps the magnetic reed switch 26 in a first disconnected state, or OFF position, which keeps the power supply 18 in electrical disconnection from the operative components 3 of the dispenser 100. Therefore, the pump 6 is inoperative, and so are the various operative components 3 of the dispenser 100.

Figure 3:
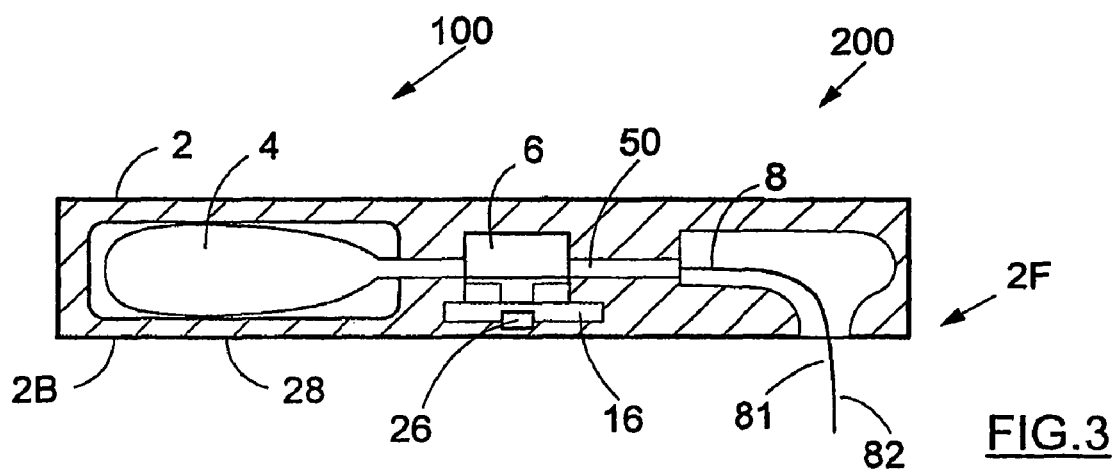
FIG. 3 shows a sectional side view of the dispenser of FIG. 1 after removal of a peel-off tape.

FIG. 3 depicts a sectional side view of the embodiment 200 after removal of the peel-off tape 22, which tape removal exposes the adhesive 28 disposed as a layer on the exterior of the housing bottom face 2B, and exposes an opening (window 21) in the housing bottom face 2B. Once exposed, the adhesive 28 allows to releasably secure the dispenser 100 to the skin S of a user U.

The removal of the peel-off tape 22 also allows the fluid delivery tool 8 to deploy in suitable extended position for insertion into the body B. The cannula 82, of the fluid delivery tool 8 protrudes to the housing exterior 2E through the window 21 opened in the housing bottom face 2B.

After the magnet 24 is removed together with the peel-off tape 22, the reed switch 26 turns into a second state, to the ON position, allowing the power supply 18 to electrically connect and energize the pump 6 as well as the operative components 3 of the dispenser 100 into operation. Because the flexible volume-conformable reservoir 4 is pressurized when full, the pump 6 is automatically primed upon initiation.

The dispenser 100 is thus ready for application by adhesive attachment to the skin S, and for simultaneous insertion of the fluid delivery tool 8 into the body B for transfusion.

Figure 4:
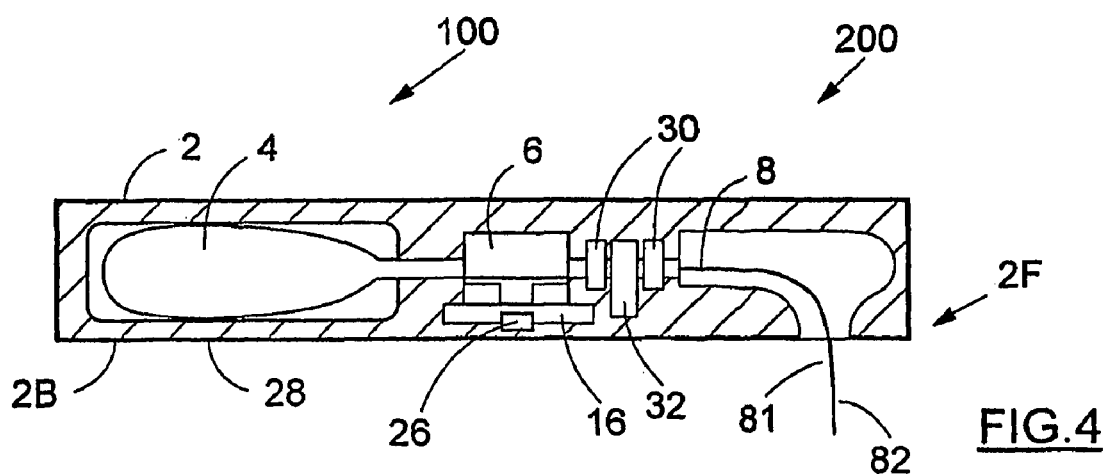
FIG. 4 shows a sectional side view of the dispenser of FIG. 1 after removal of the peel-off tape, when provided with pressure sensors and a shut-off valve according to some embodiments of the present invention.

FIG. 4 shows a sectional side-view of the embodiment 200 of the dispenser 100, after removal of the peel-off tape 22 and after activation of the fluid delivery tool 8.

The embodiment 200 is operable with either one of both or with both of two independent optional components, namely a couple of pressure sensors 30 and a shut-off valve 32.

Preferably, two or more pressure sensors 30 implemented in Micro-Electro-Mechanical Systems' technology, or MEMS, are optionally used to sense the fluid pressure at two different distanced apart points downstream of the pump 6. Two such spaced apart sensors 30 are sufficient to provide flow rate measurements, since flow rate s proportional to the pressure drop due to a flow resistance. In addition, the pressure sensors 30 may measure the backpressure, which is an important system status indicator useful, for detecting the situation when either the fluid delivery tool 8 clogs, or the pump 6 malfunctions, or there is a lack of therapeutic fluid.

A shut-off valve 32 is optionally included to prevent oozing of insulin, or other therapeutic fluid out of the dispenser 100 to the housing exterior 2E when the dispenser 100 in not operative or not in use. The shut-off valve 32 is constructed in a number of different ways. For example, but not shown in the figures, the shut-off valve 32 may be implemented as a magnetic valve, which opens upon the removal of a magnet disposed within the peel-off tape 22, in the same manner as the magnet 24 of the reed switch 26 described hereinabove. If desired, the shut-off valve 32 may be implemented as a manual valve, not shown in the figures, operated by the user U through a toggle or other mechanism after removal of the peel-off tape 22.

The reservoir 4, the fluid metering system 6, the fluid delivery tool 8 and the housing 2 will now be described in more detail. The flexible volume-conformable reservoir 4 containing the infusion fluid is preferably pre-filled by the manufacturer. The volume of the reservoir 4 is selected according to the amount of fluid to be administered during the intended period of use, which is typically up to three days long. In the case of insulin, a reservoir of 2-5 ml, preferably 3 ml is appropriate. When therapeutic fluid is injected into the reservoir 4, the reservoir expands to preferably conform to the volume of the cavities left available between the operative components 3 in the housing interior 21. The ability of the reservoir 4 to conform to irregular sizes enables optimal use of the unoccupied space left free of components in the interior of the dispenser 100, and enhances maximal miniaturization of the housing 2, thus rendering the dispenser 100 more comfortable to use. When completely full, the reservoir 4 may be sufficiently pressurized to eliminate the need for dedicated pump priming.

A positive displacement pump 6 may be used to implement the metering and dosing system, enabling precise dose control of the delivered unit quanta of fluid and the derivation of the flow rate of the therapeutic fluid. In some embodiments, the positive displacement pump 6 guarantees that the selected set point of the flow rate is held steady, irrespective of backpressure variations. In particular, in the case of insulin infusion, it is important to ensure a fluid flow that remains undisturbed by drops and variations in backpressure, as is the case for positive displacement pumps 6. A raise in backpressure may increase the insulin flow rate, which may result in insulin overdosing with ensuing hypoglycemia. Since backpressure is known to vary in response to blockage of free passage via the fluid delivery tool 8, therefore using a positive displacement pump 6 can be an important safety feature.

Figure 5A:
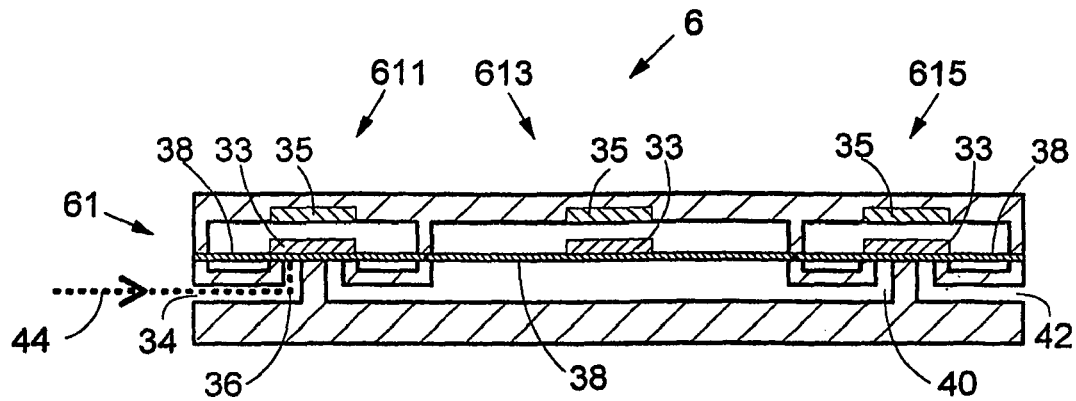
FIG. 5a is a schematic diagram of a pump and metering system shown in FIG. 1, implemented as an electromagnetic membrane pump when inactive according to some embodiments of the present invention.

FIG. 5a is a diagram of an example of one type of positive displacement pump 6 implemented as an electromagnetic membrane pump 61 having a flat layout and sheet-like planar configuration The electromagnetic membrane pump 61 has as a sequence of three cells all configured for controllable fluid flow communication, with an inlet cell 611 having a fluid inlet 34, a chamber cell 613, and an outlet cell 615 having a fluid outlet 42. All three cells, the inlet cell 611 disposed at the fluid inlet end of the electromagnetic pump 61, the intermediate chamber cell 613, and the outlet cell 615 disposed at the outlet end of the electromagnetic pump 61, respectively, have a displaceable membrane 38. Both the inlet cell 611 and the outlet cell 615 may have the same minimal volume, but the chamber cell 613, defining the dose of a unit quantum of therapeutic fluid is preferably configured according to the predetermined desired dose volume.

The membrane 38 in at least one and preferably all of cells 611, 613, and 615, carry a magnetically attractable element 33. An electromagnet 35 may also be disposed in operative association slightly away from and opposite the magnetically attractable element 33. Actuation of the electromagnet 35 lifts the membrane 38 by attraction of the attractable element 33 toward the electromagnet 35.

The inlet cell 611 and the outlet cell 615 may be configured as electromagnetically openable and closeable fluid valves 36, 40, respectively, and inlet valve 36 and outlet valve 40 may both be disposed in the normally closed state. When the inlet cell 611 resides in the normally closed state, fluid cannot pass therethrough from the fluid inlet 34 to the chamber cell 613. Likewise, when the outlet cell 615 resides in the normally closed state, fluid cannot pass therethrough from the chamber cell 613 to the fluid outlet 42. Thus, it is only when the electromagnet 35 corresponding to a specific inlet or outlet cell, namely 611 or 615, is operated that the membrane 38 is lifted, allowing fluid passage through that specific cell, by opening respectively, either the inlet valve 36 or the outlet valve 40.

When the electromagnet 35 of the chamber cell 613 is activated, then the membrane 38 is lifted, thereby enlarging the volume of that cell and permitting the ingress of liquid. Thereby, when the inlet valve 36 is open and the outlet valve 40 is closed, suction is created in the chamber cell 613 and liquid is sucked in through the fluid inlet 34. Similarly, for a closed inlet valve 36 and an open outlet valve 40, when the membrane 38 of the chamber cell 613 is pushed away from the electromagnet 35, the liquid containing volume of that cell is reduced and liquid is expelled out of chamber cell 613 and out of the fluid outlet 42. If desired, the membrane 38 in the chamber cell 613 is biased by a spring element, not shown in the figures, disposed between the electromagnet 35 and the attractable element 33 to reduce the fluid volume of that cell when the respective electromagnet 35 is deactivated.

In FIG. 5a the electromagnetic membrane pump 61 is deactivated, whereby all three electromagnets 35 are preferably inoperative. Therefore, the inlet valve 36 and the outlet valve 40 reside in the closed state, and the chamber cell, or suction cell, is disposed in the released state.

Figure 5B:
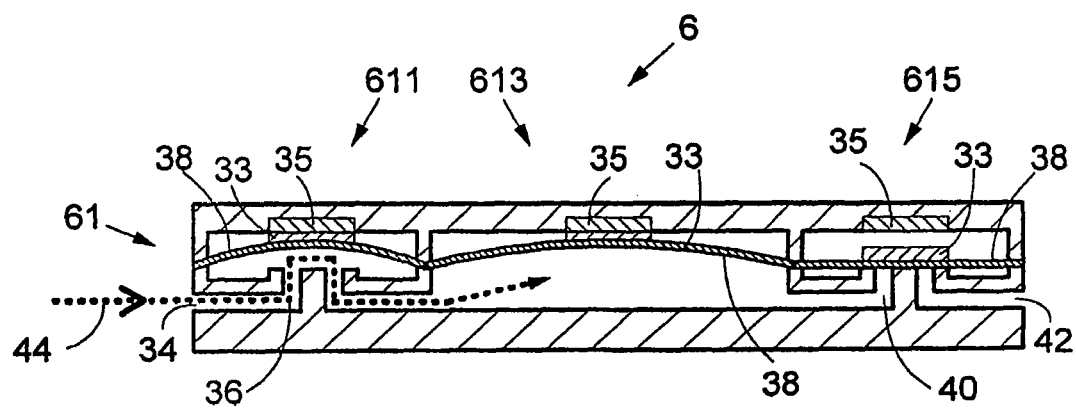
FIG. 5b shows the electromagnetic membrane pump of FIG. 5a at a suction stage.

In FIG. 5b the electromagnetic membrane pump 61 is illustrated in the suction stage. The inlet valve 36 is open and the membrane 38 is extended in outward position, in abutment with the electromagnet 35. The aspiration of fluid 44, indicated by a dotted arrow, into the pump's chamber cell 613 takes place through the pump fluid inlet 34 and the open inlet valve 36. The outlet valve 40 is closed, preventing backflow of the fluid through the pump's fluid outlet port 42 and into the pump's chamber cell 613.

Figure 5C:
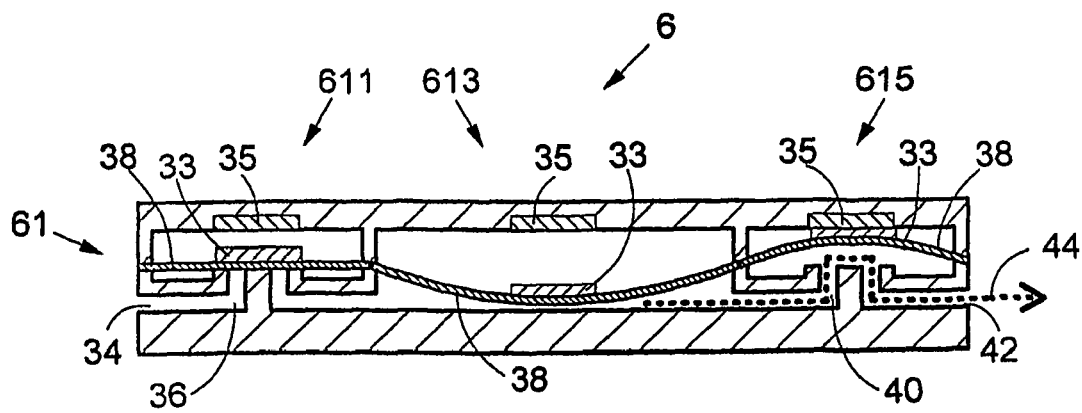
FIG. 5c shows the electromagnetic membrane pump of FIG. 5a at a discharge stage.

FIG. 5c shows the electromagnetic membrane pump 61 in a discharge stage. The inlet valve 36 is closed to prevent backflow of the pumped fluid 44, indicated by a dotted arrow, through the pump's fluid inlet port 34 toward the fluid reservoir 4. The membrane 38 is pressed toward the opposite wall of the pump's chamber cell 613, away from the electromagnet 35, thus pushing a dose of fluid 44 through the now open outlet valve 40 out of the pump 61 through the outlet port 42.

The structure of the electromagnetic membrane pump 61 may be implemented as a low profile component made of thin elements and providing a chamber cell having a minute fluid volume to permit integration in the thin low-profile housing 2. The attractable element 33, the electromagnet 35, and the membrane 38 may be considerably thin, e.g., paper-sheet thin (between about 1 micron and 10 microns). The upper and lower portions of the electromagnetic membrane pump 61 are optionally the upper and lower portions of the three cells 611, 613, and 615. Thereby the electromagnetic membrane pump 61 is about credit-card-thick at the most. To deliver larger doses than one unit quantum of therapeutic fluid, the pump 61 is operated successively.

Figure 6:
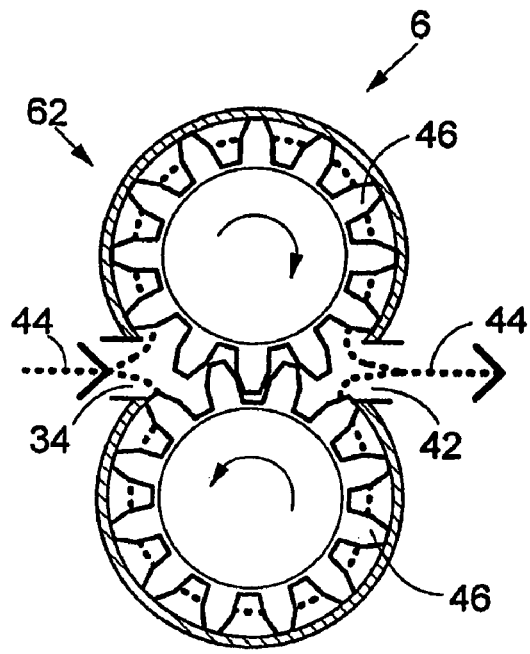
FIG. 6 illustrates a schematic diagram of a gear-on-gear pump according to some embodiments of the present invention.

FIG. 6 shows a top view of an alternative embodiment of a positive displacement pump implemented as a well-known gear-on-gear pump 62 having two gears of equal size that mesh with each other inside a case. The gear-on-gear pump 62 preferably includes a flat layout and sheet-like planar configuration. The two gears 46 mesh between the pump inlet port or fluid inlet 34 and the pump outlet port or fluid outlet 42, displacing fluid 44 toward the fluid delivery tool 8, not shown in FIG. 6, in minute, discrete, preferably equal-sized unit doses of quantum volume. The volume of a dose of fluid pumped through the gear pump 62 depends on the depth of the teeth and the width of the gear, thus on the volume of liquid retained between to adjacent teeth of the gear 46.

Flow rate may therefore be quantified, and can be precisely controlled, simply by selecting a size of the gears and teeth, and by regulating the speed of gear rotation. The flow rate preferably conforms to the following equation:

$$\text{Flow rate} = 2 * \text{rps} * N * v,$$

where:
rps—is the gear rotational speed in revolutions per second
N—is the number of teeth on each gear
v—is the discrete volume swept by a tooth Assuming, for example, that a desired basal flow rate for the infusion of insulin is 100 nanoliter/sec, then the following parameters are used for designing the pump:
Rotation rate: 1 tooth per 20 sec.
Tooth dimensions: height 0.3 mm, pitch 0.3 mm, width 1 mm Hence, the unit dose quantum of displaced volume is about 0.1 mm3, i.e. 100 nanoliter, which corresponds to the required flow rate.

For bolus delivery of insulin, the rotational speed of the gears may be increased to achieve a larger pump output dosage of more than 100 nanoliter per second over a short period of time.

Figure 7A:
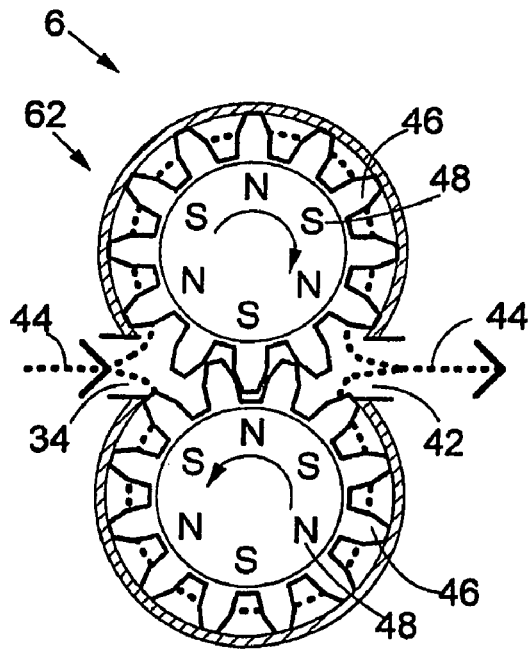
FIG. 7a is a schematic diagram of a pump and metering system shown in FIG. 1, implemented as a positive displacement gear-on-gear pump with magnetized rotors embedded in the gears according to some embodiments of the present invention.
Figure 7B:
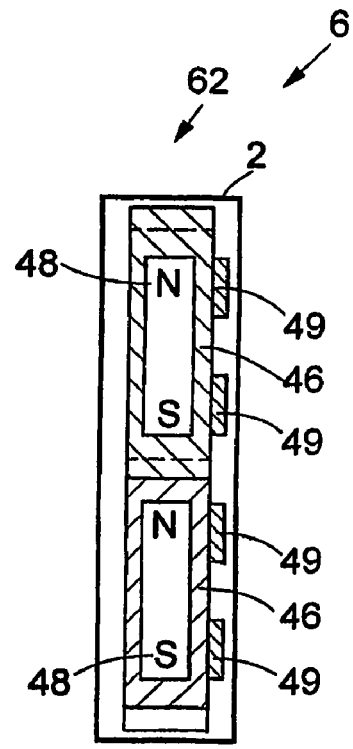
FIG. 7b is a side view of the gear-on-gear pump of FIG. 7a showing the brushless magnetic drive.

FIGS. 7a and 7b show an embodiment of a fluid metering system 6 having a gear-on-gear pump 62 as described hereinabove, driven by an integrated brushless motor with magnetic rotors 48 encapsulated in distribution in both gears 46, and with drive coils 49 appropriately disposed in the housing 2. The drive coils 49 are distributed in operative associated relationship with the magnetic rotors 48. Thereby, both gears 46 are driven gears.

FIG. 7a shows a front view of the gear-on-gear pump 62. Magnetic rotors 48 made from a magnetic material, are encapsulated in gears 46, made of plastic for example. The magnetic rotors 48 are later appropriately poled. An embodiment having only one driving gear 46 and one driven gear may also be possible.

FIG. 7b is a side view cross section of the gear-on-gear pump 62. Drive coils 49 disposed in the housing 2 operate in association with the magnetic rotors 48 to controllably rotate the plastic gears 46, under control of the programmable controller 12. Advantageously, at least one rotor position sensor 10, shown in FIG. 1, may be used to provide information about the gears' rotation speed, wherefrom the programmable controller 12 derives the dispensed fluid flow rate. A suitable sensor may be a Hall effect sensor.

If desired, the rotational speed of the plastic gears 46, as derived by the position sensor 10, may be used for direct control of the flow rate of the therapeutic fluid 44. As described hereinabove, the position sensor 10 may be disposed on the PCB 161, or on the integrated circuit 162, or elsewhere within the housing 2.

Figure 8:
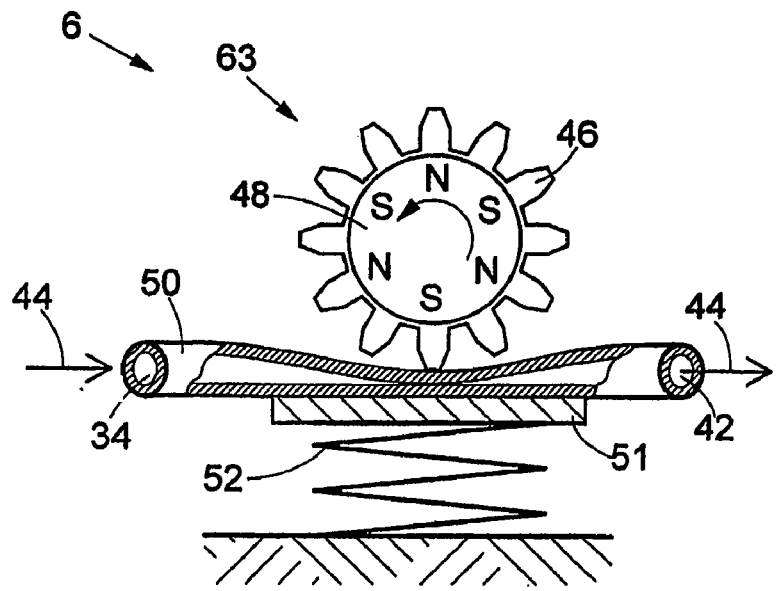
FIG. 8 is a schematic diagram of a pump and metering system, shown in FIG. 1, implemented as a single-gear pump and a counter-plate according to some embodiments of the present invention.

FIG. 8 shows a pump 6 embodiment which may also be operative as a dosing and metering system, comprising a single-gear peristaltic pump 63 having an integrated brushless motor, and having a flat layout and sheet-like planar configuration. Accordingly, the single gear 46 of the pump 63 squeezes one side of a fluid-conducting tube 50, which is preferably a flexile and resilient tube extending between the reservoir 4 and the fluid delivery tool 8. The peristaltic pump 63 squeezes the tube 50 against a counter-plate 51 disposed on the opposite side of the tube 50. An elastic member, for example a spring 52, may be used to bias the counter plate 51 onto the tube 50. In this embodiment too, the magnetic rotors 48 may be embedded or encapsulated into the single plastic gear 46. The magnetic rotors 48 are poled appropriately to be driven by coils 49, not shown in FIG. 8, and to function as a motor. This is achieved by appropriately distributing the plurality of rotors 46 in operative associated relationship with the distribution of the plurality coils 49.

In both embodiments the electric drive coils 49 may be operated under control and command of the programmable controller 12 to drive the at least one gear 46 into controlled rotation. The implementation of the motor for driving the single-gear peristaltic pump 63 may be the same as that for the gear-to-gear pump 62. It is noted that the gear-to-gear pump 62 is possibly implemented with a single motor-driven gear 46, in the same manner as for the single-gear peristaltic pump 63, or with two driven gears 46 (for example).

The fluid flow rate of the single-gear pump 63 may be expressed as:

$$\text{flow rate} = rps * N * v * \eta$$

where
rps is the gear speed in revolutions per second,
N is the number of teeth on the gear,
v is the volume swept by each tooth of the gear 46, and
η is the volumetric efficiency.

Accordingly, further to the above-noted equation, the flow rate is the aggregate of the minute quanta unit doses of fluid, defined by the gears 46 and the translation of the teeth distributed thereon on the tube 50, and may be precisely controlled by regulating the speed of gear rotation. In practice a dosing and metering pump 6 may be configured to deliver a single minute unit quantum dose of predetermined volume as small as 10 nanoliters, or less (e.g., between about 1 nanoliter and 100 nanoliters or more). The dose of a quantum unit delivered is preferably predetermined according to the distribution, configuration, and dimensions of the gear 46 and their gear teeth, including the width of the gear, and the speed of rotation imparted to the gear 46, as described hereinabove.

Alternative embodiments of gear pumps suitable as a pump and metering system 6 for the dispenser 100 may employ a miniature gear motor to drive the pump 6, such as a dish motor of flat shape, not shown in the figures.

In one embodiment of the dispenser 100, the fluid delivery tool 8 may be fitted with an elastic folding miniature low gauge trocar 81 surrounded by a flexible cannula 82. In such an embodiment, the cannula 82 is configured to automatically emerge through the window 21 opened in the bottom of the housing 2 when the peel-off tape 22 is removed and to extend to the housing exterior 2E. When the dispenser 100 is secured to the skin S, the trocar 81, possibly hollow, pierces the skin S and penetrates the body B, whereafter the trocar 81 may be retracted leaving the cannula 82 properly inserted. If desired, the fluid delivery tool 8 may only include a cannula 82 without a trocar 81. The cannula 82 may be made of metal or of plastic, as desired.

In other preferred embodiments of the dispenser 100, not shown in the figures, the fluid delivery tool 8 is a plastic cannula 82 that is inserted into the body B through the skin S of the user U by means of an insertion mechanism. The cannula 82 is driven into the skin S by a sharp penetration member, such as a solid or hollow trocar 82, made of a flexible metallic material that is inserted in the interior of the cannula lumen. When the insertion mechanism is activated, the penetration member is pushed into the skin S together with the cannula 82 and penetrates the body B. After penetration, the penetration member is retracted into the housing 2, while the retraction of the cannula 82 into the housing 2 is prevented, whereby the cannula 82 remains inserted into the body B.

Turning to another aspect, it is well known that cooling can ease the local pain at an injection site. Therefore, it is advantageous to store the dispensers 100, or insulin dispensers 100 in refrigeration until use. To that end, a metallic ring 66 having a predetermined thermal capacity mass to absorb cold may be disposed to surround the window 21 open on the housing bottom face 2B and is cooled prior to application and use of the dispenser 100, as a means for cooling the skin S on contact. Accordingly, application of the dispenser 100 with the cooled metallic ring 66 in contact with the skin S at the penetration site eases pain caused by insertion of the fluid delivery tool 8.

In practice, the housing 2 may be fabricated from a suitable plastic material. For insulin delivery, for example, a plastic material that does not cause insulin polymerization is used. In one preferred embodiment the housing 2 is shaped as a flat normal parallelepiped box. The dimensions of the box may vary, but a typical size for an insulin dispenser 100 are about 50×30×4 mm, i.e. 50 mm in length (less than 50 to about 75 mm), 30 mm in width (less than 30 to about 60 mm) and 4 mm in thickness (less than about 4 mm to about 10 mm or more), with a reservoir 4 having a volume of 3 cc (1 cc-10 cc). Other housing 2 embodiments may have the same planar surface and the same thickness as the typical size of a parallelepiped box described hereinabove, but instead of having a rectangular surface may have other geometrical shapes such as an ellipse, a circle, a polygon, a crescent, and the like, as desired. Typically, the planar surface of the housing is 1500 mm$^2$ (less than 1500 to about 4500 mm$^2$).

Accordingly, in some embodiments of the invention, an insulin dispenser 100 may be about half the size of a credit card and only about as four times as thick. It is beneficial to appropriately reinforce and provide rigidity to the dispenser 100 at specific locations thereon to avoid impairment of operation due to pressure caused, for example, when the user U sleeps on the device and rests thereon with all his weight. Furthermore, it is beneficial to impart appropriate flexibility to allow conformance of the housing 2 with the curvatures of the body B.

The operative components 3 of the dispenser 100 may be appropriately configured and disposed therein in a planar/flat layout to minimize the external dimensions of the housing 2. Although only depicted symbolically in FIG. 1, suitable mounting seats 64 may be disposed in the housing interior 2I to support and receive thereon the operative components 3 of the dispenser 100, such as the pump 6, the electronic circuit 16, the power supply 18, and the other components. After the operative components 3 are properly mounted, the housing 2 is permanently closed and sealed to look like half a thick credit card.

In accordance with one of the embodiments of the invention, there is a transparent pane not shown in the figures, covering the user interface unit 15, where through visual outputs, such as LED lights, are viewed. Another portion of the transparent pane of the user interface unit 15 may be substantially thin enough so as to be flexible and allow depression of the keys of a keyboard. Moreover, provision is made for an alarm signal to be heard, such as sounded by a buzzer and the like.

It is appreciated that the dispenser 100 may be of simple and straightforward design, and is configured for ease of manufacturing thereby keeping production costs low, which in its turn justifies discarding the dispenser 100 after use, as a disposable item.

After assembly of the housing 2, the therapeutic fluid may be injected into the reservoir 4 and the window 21 which is open in the housing bottom face 2B is ready for final sealing. In turn, peel-off tape 22 may be attached to the housing bottom face 2B either before or after filling the reservoir 4. It is beneficial, however, to seal the tape 22 before filling the reservoir 4, since this ensures fluid sterility.

Figure 9:
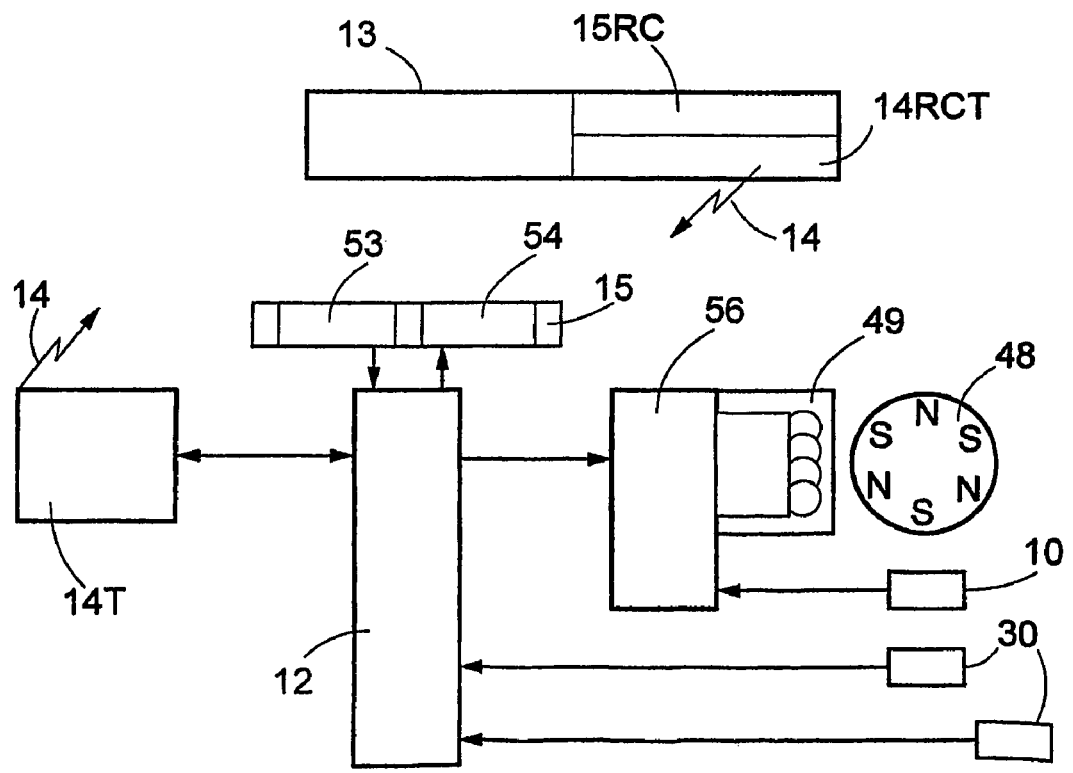
FIG. 9 depicts a block diagram of the dispenser' control system shown in FIG. 1 according to some embodiments of the present invention

FIG. 9 is an exemplary block diagram of an embodiment of the control system of the dispenser 100 having for example, a single-gear pump 63 or another magnetic positive displacement pump 6.

As shown in FIG. 9, the controller 12 receives flow rate data and commands from the remote control device 13 through the communication channel 14 or alternatively, from the user interface unit 15, e.g. the I/O unit having, say, a keypad 53. The controller 12 generates command signals for delivery to the drive coils 49 operating the magnetic rotor 48 through a commutator 56. These command signals are based on commutation signals obtained from the position sensors 10 that indicate the instantaneous position of the magnetic poles of the rotor 48 vis-à-vis the drive coils 49, as is well known in the art of brushless motor design. The controller 12 receives fluid pressure data from the pressure sensors 30, compares the received pressure data and the derived fluid flow rate data against the programmed parameters, to correct pump 6 output and generate alarms if necessary. The dispenser status information is transmitted to the remote control device 13 through the communication channel 14, and this status information is optionally displayed on a display 54 disposed on the user interface unit 15 and/or on the remote control I/O user interface 15RC.

The dispenser 100 system 1000 thus has a remote control device 13 including a remote control transceiver 14RCT operating the bi-directional communication channel 14 for interactive communication with the programmable controller 12, and a remote control I/O user interface 15RC disposed on the transceiver 14RCT and operable by the user U for entering and receiving data, instructions and commands, respectively to and from the programmable controller 12.

Once used and empty, or when desired, the disposable dispenser 100 is safely discarded as described hereinbelow.

Figure 10A:
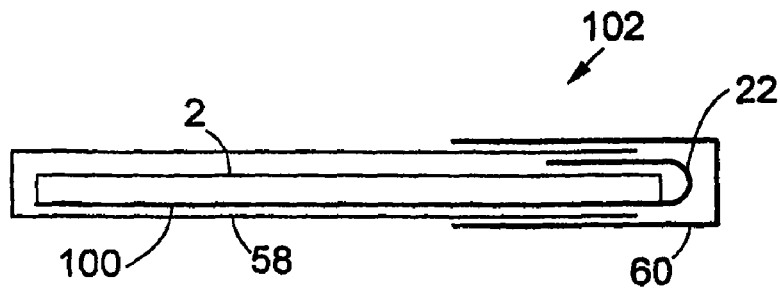
FIG. 10a shows the dispenser of FIG. 1 before use, when packed in a box.

FIG. 10*a* shows an example of a single dispenser 100 as packaged for supply to a user U. The housing 2 with the peel-off tape 22 attached thereto and prior to use, is stored in a box 58, or package 58, which is closed by a removable cover 60. For use, the cover 60 is removed from the box 58 and the dispenser 100 is retrieved out of the box 58, whereafter the fluid delivery tool 8 unfolds, deploys and extends to protrude to the housing exterior 2E, in ready position for insertion into the body B.

The box 58 and the cover 60 constitute together a single packaged dispenser 102. Several individually packaged dispensers 102 may also be available as a kit. Such a kit is suitable as a supply of therapeutic fluid for a predetermined period of time.

Figure 10B:
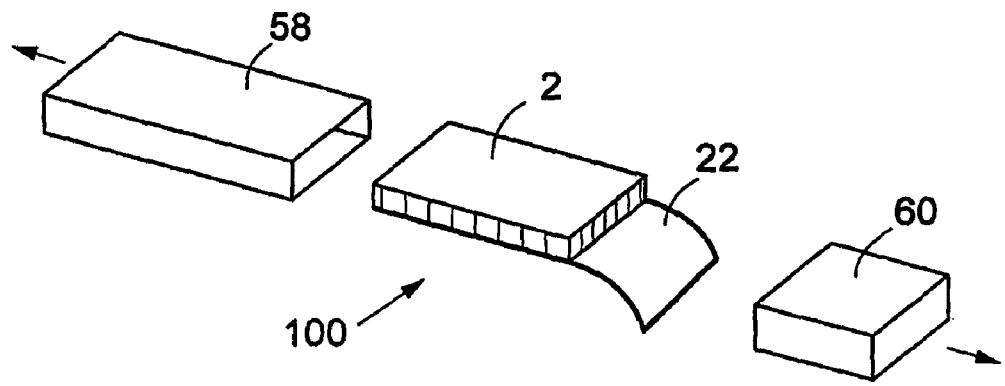
FIG. 10b shows the dispenser of FIG. 1 when it is taken out of the box.

FIG. 10*b* shows the dispenser 100 after retrieval from the box 58, which retrieval is achieved by pulling the cover 60 away from the box 58.

Figure 10C:
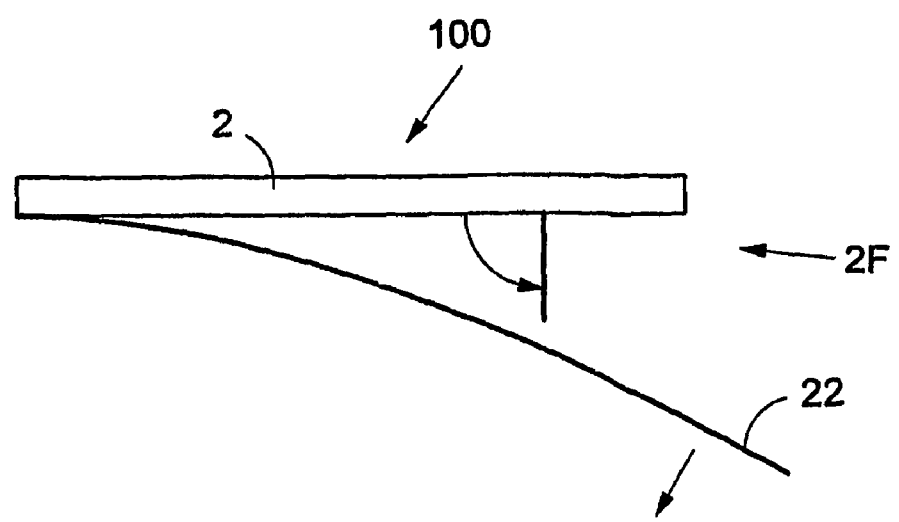
FIG. 10c shows removal of the peel-off tape from the dispenser of FIG. 1.

In FIG. 10*c* the dispenser 100 is shown out of the box 58 and ready for use, before the peel-off tape 22 is pulled away from housing 2. Since the fluid delivery tool 8 is flexible, removal of the peel-off tape 22 causes the foldable cannula 82 to automatically unfold, straighten up and extend so as to protrude out to the exterior of the housing 2. In accordance with alternative embodiments, the fluid delivery tool 8 may protrude out of the housing 2 only after activation of a locking mechanism releasing the cannula 82.

Figure 11A:
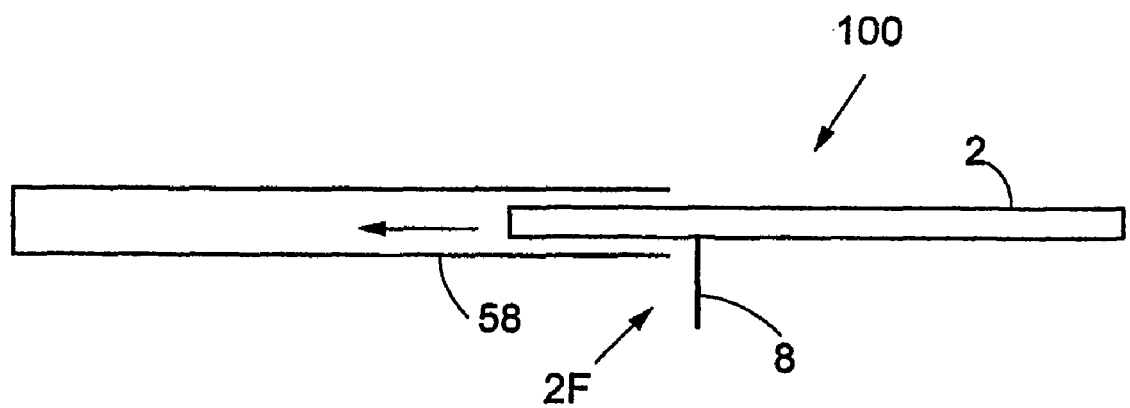
FIG. 11a shows insertion into a box of the dispenser of FIG. 1.

FIG. 11 illustrates a method for the safe disposal of a dispenser 100, when desired or when depleted, by re-insertion of the dispenser 100 into its box 58. The fluid delivery tool 8 which is carried closer to the front of the housing 2, on the housing front side 2F, is introduced first into the box 58. Due to flexibility, the fluid delivery tool 8 folds to a collapsed position alongside the housing bottom face 2B. Thereafter, the box 58 is closed with the cover 60.

Figure 11B:
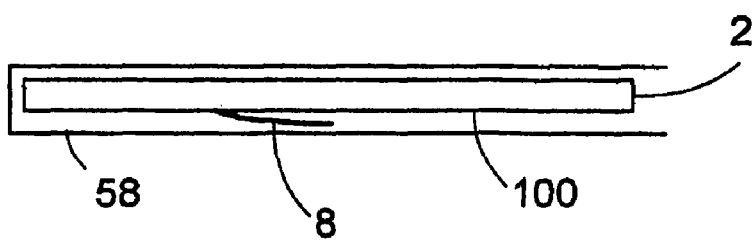
FIG. 11b shows the dispenser of FIG. 1 when spent and fully inserted into a box before closure of the cover.

FIG. 11*b* shows a used dispenser 100 repackaged for disposal. The housing 2 is completely enclosed in the box 58 and the fluid delivery tool 8 is also safely tucked into the box 58, after being folded along the box 58, eliminating contamination hazards. Next, the box 58 is closed with the cover 60.

There is also provided a system 1000 for patient infusion with a disposable dispenser 100 as described hereinabove, having an external remote control device 13 that can be programmed through a remote control I/O user interface 15RC. The dispenser 100 and the programmable controller 12 communicate through the bi-directional communication channel 14, via the remote control transceiver 14RCT and the transceiver 14T, with respective modulator and demodulator devices operative for bi-directional communication. The bidirectional communication channel 14 is also used as a communication link with other external control and communication modalities and/or with archive facilities.

In operation, the use of the system 1000 and of the dispenser 100 for patient infusion is very simple: a patient or user U operates the remote control device 13 that is programmed with his/her individual treatment parameters.

In addition, the patient may obtain a kit that contains several individually packaged disposable dispensers 100, providing a supply of medication for a predetermined period of time. To use a dispenser 100, the patient U removes the cover 60 from the box 58 to retrieve the dispenser 100 therefrom, and then removes the peel-off tape 22. Removal of the peel-off tape 22 exposes the adhesive 28, and allows electrical connection of the power supply 18, or battery 18, thereby powering the operative components 3 of the dispenser 100 into operation.

In one embodiment of the dispenser 100, the fluid delivery tool 8 has a foldable cannula 82 that is automatically released to extend to the housing exterior 2E upon removal of the peel-off tape 22 and unfolds ready for immediate insertion into the skin S of a user U. In other embodiments, the delivery tool 8 emerges from the housing only after activation of an insertion mechanism.

Optionally, toggling of an additional shut-off valve 32 is required to initiate the dispenser 100.

Next, the patient U applies the dispenser 100 where desired on the skin S of his body B. By firmly applying and pressing the entire housing bottom face 2B onto the skin S, the adhesive 28 adheres to the desired body-location whereto it remains attached during the whole period of infusion.

In those embodiments in which the fluid delivery tool 8 self-unfolds and extends, application and pressing of the dispenser 100 onto the body B preferably forces the cannula 82 to penetrate through the skin S and enter into the body B. In other embodiments the delivery tool 8 requires the operation of an insertion mechanism, which drives the cannula 82 together with its trocar 81 into the skin S. The trocar 81 is then retracted into the housing 2 and the dispenser 100 is ready for infusion.

In use, a command signaling the flow rate set point may be sent to the controller 12 through the communication channel 14. The fluid flow rate is regulated through the dispenser's user interface unit 15, or by the remote control device 13 which may be preprogrammed or manually operated. At the end of the designated period of use, typically up to three days, the dispenser 100 is removed from the body B and reinserted into its box 58 for safe disposal.

It will be appreciated by persons skilled in the art, that the present invention is not limited to what has been particularly shown and described. The preceding description and attached figures cover more than the described embodiments and permits various alternative embodiments that are not described. Rather, the scope of the present invention is defined by the appended claims and includes both combinations and subcombinations of the various features described hereinabove as well as variations and modifications thereof which would occur to persons skilled in the art upon reading the foregoing description.

The invention claimed is:

1. A disposable therapeutic fluid dispenser having a thin flat planar construction for infusing a therapeutic fluid through the skin into the body of a user, the dispenser comprising:
   a housing;
   a power supply;
   a reservoir;
   a pump;
   a window provided on a first side of the housing;
   a fluid delivery tool, the fluid delivery tool being fluidly coupled to the pump and being insertable through the window into the body of the user to deliver one or more controlled doses of therapeutic fluid to the user; and
   removable tape arranged on the first side of the housing and configured upon removal to:
      expose the window for insertion of the fluid delivery tool therethrough into the body of the user; and
      enable the supply of power for operation of the fluid dispenser.

2. The disposable therapeutic fluid dispenser according to claim 1, wherein
   said pump is a peristaltic pump arranged within an interior of the housing, the peristaltic pump comprising a motor and a gear, and
   a counter plate provided on a second side of a fluid delivery tube opposite a first side of the fluid delivery tube which is positioned adjacent to the gear.

3. The disposable therapeutic fluid dispenser according to claim 2, wherein the peristaltic pump is a single gear pump.

4. The disposable therapeutic fluid dispenser according to claim 2, further comprising a gear position sensor disposed within the housing interior in operative association with the pump, and coupled to the controller to derive the flow rate of the therapeutic fluid.

5. The disposable therapeutic fluid dispenser according to claim 2, further comprising at least two pressure sensors disposed within the housing interior said sensors are spatially arranged downstream of the pump and upstream of the fluid delivery tool, and said sensors are coupled to the controller to derive either one of fluid flow rate and fluid flow pressure or both fluid flow rate and fluid flow pressure.

6. The disposable therapeutic fluid dispenser according to claim 1, wherein:
   the pump has at least one gear with distributed therein a plurality of magnetic rotors, a plurality of electric drive coils distributed within the housing interior in accordance with the plurality of magnetic rotors, wherein the electric drive coils are controllable by the controller to rotate the at least one gear.

7. The disposable therapeutic fluid dispenser according to claim 6, wherein the electric drive coils are controllable by the controller to rotate the single gear at a pre-determined speed of rotation; and the dose supplied by the pump is predetermined according to the configuration of the gear and of the speed of rotation of the gear.

8. The disposable therapeutic fluid dispenser according to claim 6, further comprising a gear position sensor disposed within the housing interior in operative association with the pump, and said sensor is coupled to the controller to derive the flow rate of the therapeutic fluid.

9. The disposable therapeutic fluid dispenser according to claim 6, further comprising at least two pressure sensors said sensors are disposed within the housing interior spatially arranged downstream of the pump and upstream of the fluid delivery tool, and said sensors are coupled to the controller to derive either one of fluid flow rate and fluid flow pressure or both fluid flow rate and fluid flow pressure.

10. The disposable therapeutic fluid dispenser according to claim 1, wherein said pump is a gear-on-gear pump.

11. The disposable therapeutic fluid dispenser according to claim 10, further comprising a gear position sensor disposed within the housing interior in operative association with the pump, and said sensor is coupled to the controller to derive the flow rate of the therapeutic fluid.

12. The disposable therapeutic fluid dispenser according to claim 10, further comprising at least two pressure sensors said sensors are disposed within the housing interior spatially arranged downstream of the pump and upstream of a fluid delivery tool, and said sensors coupled to the controller to derive either one of fluid flow rate and fluid flow pressure or both fluid flow rate and fluid flow pressure.

13. The disposable therapeutic fluid dispenser according to claim 1, wherein said pump is electromagnetic membrane pump.

14. The disposable therapeutic fluid dispenser according to claim 13, further comprising at least two pressure sensors disposed within the housing interior said sensors are spatially arranged downstream of the pump and upstream of a fluid delivery tool, and said sensors are coupled to the controller to derive either one of fluid flow rate and fluid flow pressure or both fluid flow rate and fluid flow pressure.

15. The disposable therapeutic fluid dispenser according to claim 1, wherein the fluid delivery tool is capable of being arranged in a collapsed position upon being placed in a package, and wherein upon removing the dispenser from the package, the fluid delivery tool is capable of unfolding to protrude to the housing exterior and thereby be ready for insertion into the body of the user.

16. The disposable therapeutic fluid dispenser according to claim 15, wherein the fluid delivery tool is capable of being re-collapsed for placement into a package for disposal.

17. The disposable therapeutic fluid dispenser according to claim 1, further comprising a controller for at least one of control, management and operation of the dispenser wherein upon removal of the tape, power is supplied to at least one of the controller and the pump to enable operation of the fluid dispenser.

18. A method for operating a disposable therapeutic fluid dispenser having a thin flat planar construction for infusing a therapeutic fluid through the skin into the body of a user, comprising:
   providing a therapeutic fluid dispenser, the fluid dispenser comprising:
   a housing;
   a power supply;
   a reservoir;
   a pump;
   a window provided on a first side of the housing;
   a fluid delivery tool, the fluid delivery tool being fluidly coupled to the pump and being insertable through the window into the body of the user to deliver one or more controlled doses of the therapeutic fluid; and
   a removable tape arranged on the first side of the housing; and
   exposing the window for insertion of the fluid delivery tool therethrough into the body of the user by removing the tape, wherein removal of the tape also results in power being supplied for operation of the fluid dispenser.

19. The method according to claim 18, wherein the fluid dispenser further comprises a controller for at least one of control, management and operation of the dispenser, and wherein upon removal of the tape, power is supplied from the power supply to at least one of the pump and controller to enable operation of the fluid dispenser.

* * * * *